(12) United States Patent
Barbedette et al.

(10) Patent No.: US 11,305,026 B2
(45) Date of Patent: Apr. 19, 2022

(54) SYSTEMS AND APPROACHES FOR STERILIZING A DRUG DELIVERY DEVICE

(71) Applicant: AMGEN INC., Thousand Oaks, CA (US)

(72) Inventors: Loic Barbedette, Newbury Park, CA (US); Shaun Devitt, Wayne, PA (US); Wael Mismar, Redondo Beach, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 16/179,450

(22) Filed: Nov. 2, 2018

(65) Prior Publication Data

US 2019/0134296 A1   May 9, 2019

Related U.S. Application Data

(60) Provisional application No. 62/581,379, filed on Nov. 3, 2017.

(51) Int. Cl.
*A61M 5/00* (2006.01)
*A61L 2/26* (2006.01)
(Continued)

(52) U.S. Cl.
CPC .................. *A61L 2/08* (2013.01); *A61L 2/081* (2013.01); *A61L 2/087* (2013.01); *A61L 2/26* (2013.01);
(Continued)

(58) Field of Classification Search
None
See application file for complete search history.

(56) References Cited

U.S. PATENT DOCUMENTS

| 4,850,484 A | 7/1989 | Denman |
| 5,129,886 A | 7/1992 | Sincock |

(Continued)

FOREIGN PATENT DOCUMENTS

| WO | WO-2005/032627 A1 | 4/2005 |
| WO | WO-2007/024957 A1 | 3/2007 |

(Continued)

OTHER PUBLICATIONS

International Application No. PCT/US2018/058970, International Search Report and Written Opinion, dated Mar. 1, 2019.

(Continued)

*Primary Examiner* — Michael J Logie
(74) *Attorney, Agent, or Firm* — Marshall, Gerstein & Borun LLP

(57) ABSTRACT

A shielding member for use in sterilizing drug container assemblies includes a housing. The housing includes a first shielding portion and a second shielding portion. The first shielding portion includes a first and second surfaces and a plurality of first bore portions extending between. The second shielding portion having a first and second surfaces and a plurality of second bore portions corresponding to and aligned with the plurality of first bore portions. The first and second bore portions cooperate to form a plurality of receptacles including a plurality of openings in the first surface of the first shielding portion of the housing. The receptacles are sized and configured to receive drug container assemblies, each comprising a container with a container contact region and a seal member disposed adjacent the container contact region to seal the contents of the container at a sealing interface, such that each drug container assembly is exposed out of the housing through one of the openings.

19 Claims, 7 Drawing Sheets

(51) Int. Cl.
*A61L 2/08* (2006.01)
*A61M 5/28* (2006.01)
*B65B 3/00* (2006.01)
*B65B 55/08* (2006.01)
*G21F 1/02* (2006.01)
*G21F 1/06* (2006.01)
*G21F 1/08* (2006.01)

(52) U.S. Cl.
CPC ............ *A61M 5/008* (2013.01); *A61M 5/285* (2013.01); *B65B 3/003* (2013.01); *B65B 55/08* (2013.01); *G21F 1/02* (2013.01); *G21F 1/06* (2013.01); *G21F 1/08* (2013.01); *A61L 2202/23* (2013.01); *A61M 5/001* (2013.01); *A61M 5/002* (2013.01)

(56) References Cited

U.S. PATENT DOCUMENTS

| | | | |
|---|---|---|---|
| 5,167,816 A | | 12/1992 | Kruger et al. |
| 6,030,578 A | | 2/2000 | McDonald |
| 6,221,216 B1 | * | 4/2001 | Nablo .................... A61L 2/08 204/157.15 |
| 2004/0141886 A1 | | 7/2004 | Py et al. |
| 2005/0133729 A1 | | 6/2005 | Woodworth et al. |
| 2006/0076520 A1 | * | 4/2006 | Drobnik ................ A61L 2/07 250/506.1 |
| 2006/0151714 A1 | * | 7/2006 | Thilly .................. A61L 2/0011 250/453.11 |
| 2007/0053788 A1 | | 3/2007 | Zhao |
| 2011/0002821 A1 | | 1/2011 | Hyde et al. |
| 2014/0027332 A1 | | 1/2014 | Pawlowski et al. |
| 2015/0182686 A1 | * | 7/2015 | Okihara ............ B65D 77/2024 206/366 |
| 2015/0190566 A1 | * | 7/2015 | Okihara ................ A61M 5/002 206/365 |
| 2016/0213796 A1 | | 7/2016 | Kohara et al. |
| 2016/0296704 A1 | * | 10/2016 | Gibson ............... A61M 5/1782 |
| 2018/0133396 A1 | * | 5/2018 | McLaughlin ..... A61M 5/16827 |
| 2019/0038790 A1 | * | 2/2019 | McLaughlin ........... A61L 2/206 |
| 2019/0134296 A1 | | 5/2019 | Barbedette et al. |
| 2019/0135471 A1 | * | 5/2019 | Barbedette ............. B65B 3/003 |
| 2019/0167895 A1 | * | 6/2019 | Dechelette .......... A61M 5/1452 |

FOREIGN PATENT DOCUMENTS

WO  WO-2011/110872 A1  9/2011
WO  WO-2014/112113 A1  7/2014

OTHER PUBLICATIONS

U.S. Appl. No. 16/813,365, Nonfinal Office Action, dated Apr. 15, 2020.
U.S. Appl. No. 16/813,365, Final Office Action, dated Jul. 21, 2020.
U.S. Appl. No. 16/179,399, Nonfinal Office Action, dated Jun. 25, 2020.

* cited by examiner

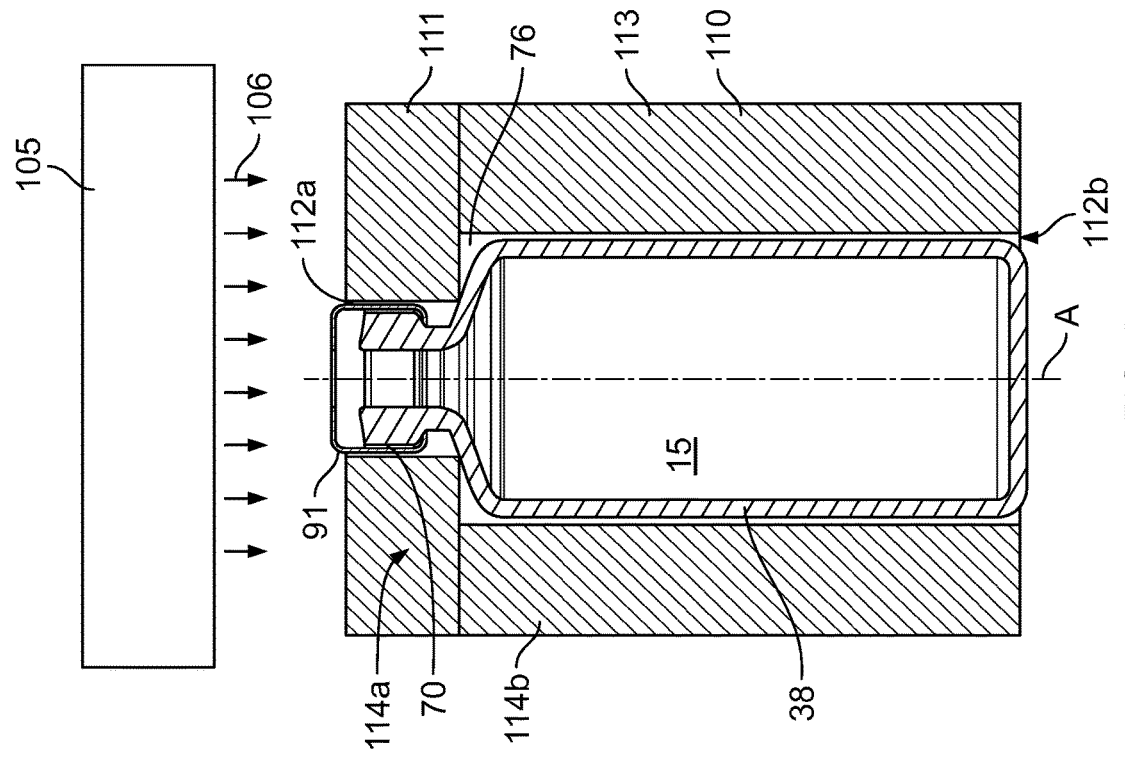
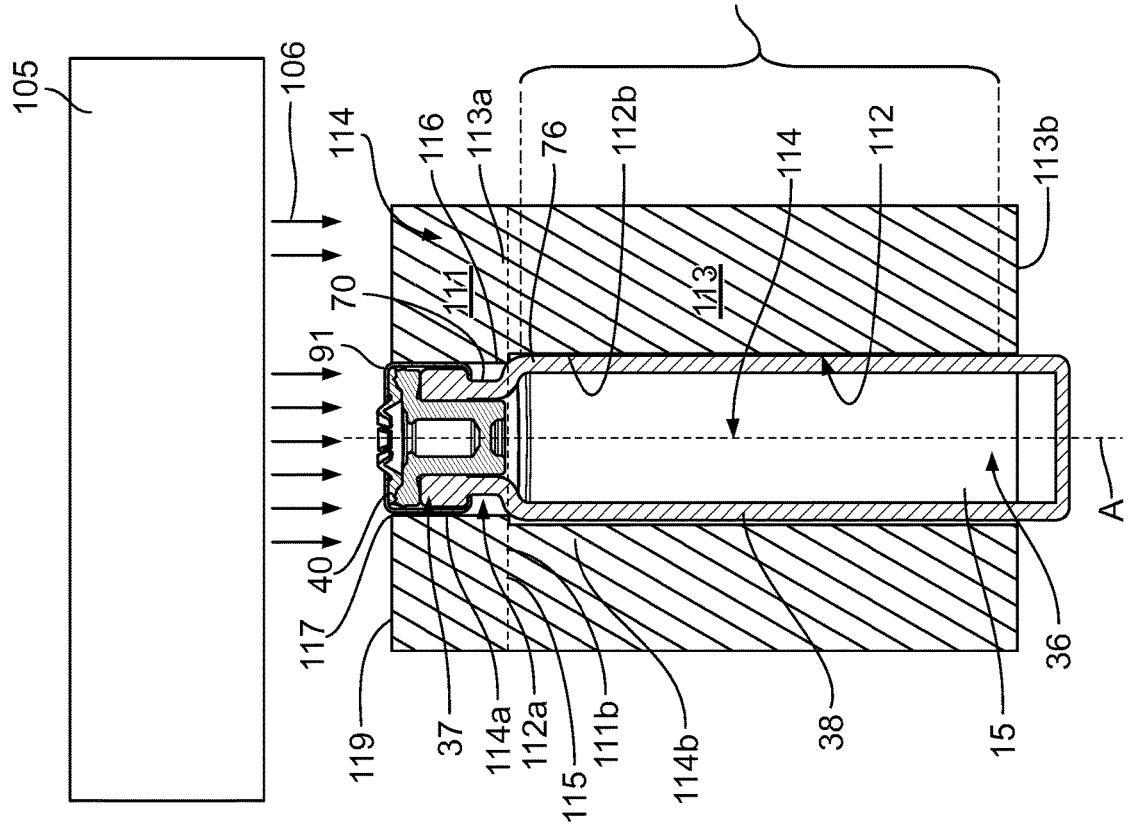

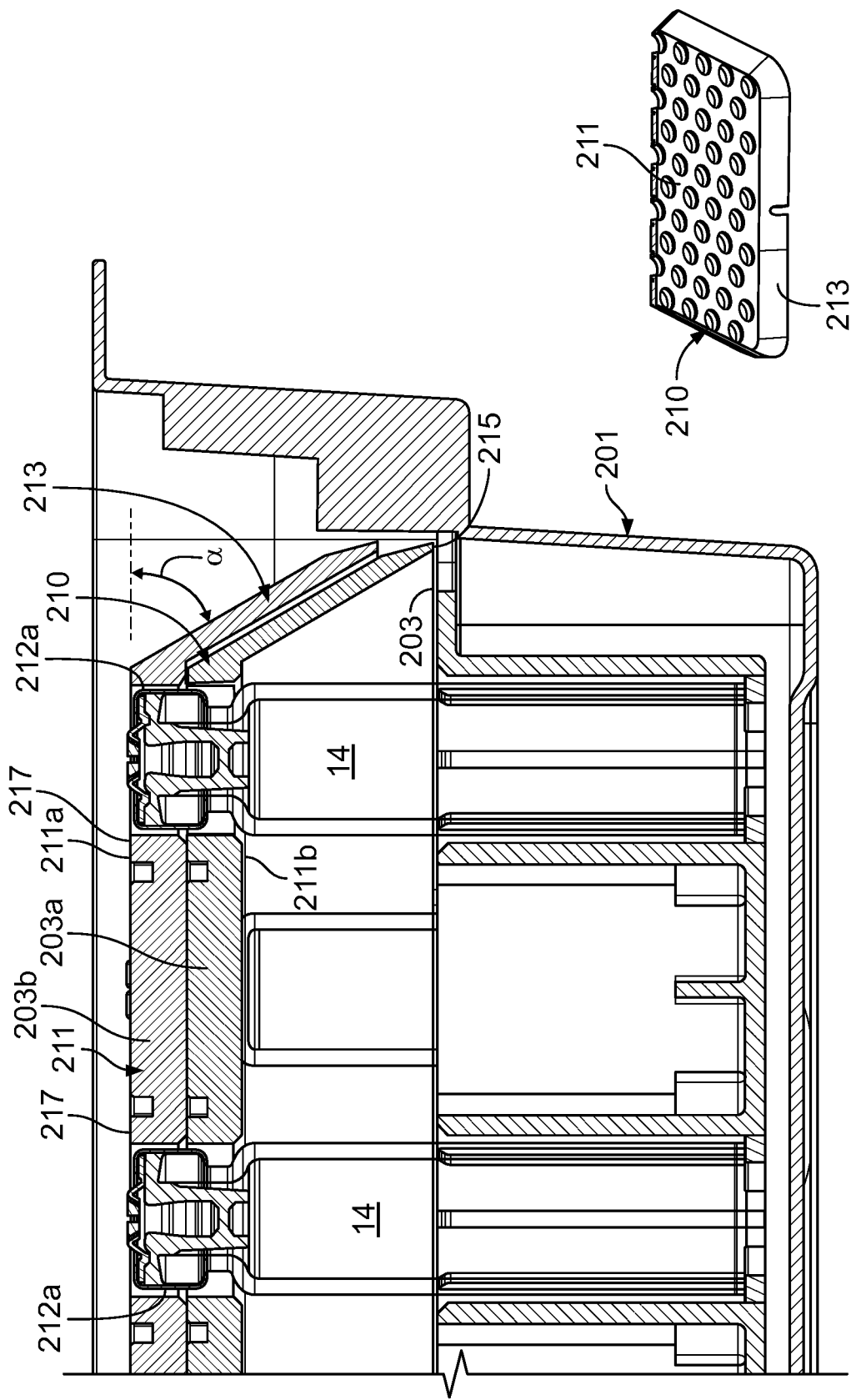

SYSTEMS AND APPROACHES FOR STERILIZING A DRUG DELIVERY DEVICE

CROSS-REFERENCE TO RELATED APPLICATIONS

Priority is claimed to U.S. Provisional Patent Application No. 62/581,379, filed Nov. 3, 2017, the entire contents of which are hereby incorporated herein by reference.

FIELD OF THE DISCLOSURE

The present disclosure generally relates to drug delivery devices and, more particularly, to enabling a sterile drug container assembled within a drug delivery device.

BACKGROUND

Drug delivery devices, such as injectors, are used to deliver liquid drugs to a patient. Upon activation, a drug delivery device will expel a drug stored within an internal reservoir through a needle, cannula, or other delivery member into the patient. Certain drug delivery devices are manufactured with an empty reservoir, and the patient or healthcare provider (e.g., a doctor, nurse, healthcare assistant, etc.) will fill the reservoir with the drug at the time of use. Typically, this requires the patient or healthcare provider to operate a syringe to inject the drug into the empty reservoir through an inlet port formed in the drug delivery device. Prior to this filling procedure, the inlet port should be sterilized by swabbing its outer surface with an alcohol wipe, for example. Alternatively, certain drug delivery devices are installed with a pre-filled drug container by the patient or healthcare provider at the time of use. Before installing the pre-filled drug container, mating connectors disposed on, respectively, the pre-filled drug container and a fluid pathway assembly within the device should be sterilized, for example, by swabbing them with an alcohol wipe. In either case, the drug delivery device must be prepared by the patient or healthcare provider prior to use.

More recently, drug delivery devices have become available which are pre-assembled with a pre-filled drug container. This alleviates the patient or healthcare provider from having to add the drug to the drug delivery device at the time of treatment. In such drug delivery devices, a sterile fluid flow path is established between the pre-filled drug container and a fluid pathway assembly upon activation of the device. Generally, this involves accessing an interior of the drug container with a container access needle such that the drug can be expelled from the container via the container access needle. Prior to activation of the device, the container access needle should be maintained in a sterile condition so that the container access needle does not introduce contaminants into the container upon activation of the device. In some approaches, existing assemblies for creating a sterile environment for the drug container may be incapable of adequately sterilizing required components and/or desired surfaces. For example, a gaseous sterilizing mixture (such as, for example ethylene oxide and/or saturated steam) may be incapable of adequately penetrating or permeating through components in order to adequately sterilize certain components. In other examples, some existing approaches may also negatively impact the appearance or structural integrity of the container, or alternatively may adversely impact the drug itself. In these examples, a user or healthcare provider may need to visually inspect the device to ensure that there are no potentially hazardous contaminants in the container. In the event that the appearance and/or structural integrity of the container may be compromised, it may be difficult or impossible to conduct visual inspections, and thus, containers may be preemptively unnecessarily disposed of.

The present disclosure sets forth systems and approaches for sterilization of drug delivery devices and related methods of assembly and sterilization embodying advantageous alternatives to existing sterilization systems and methods, and that may address one or more of the challenges or needs mentioned herein, as well as provide other benefits and advantages.

SUMMARY

One aspect of the present disclosure provides a shielding member for use in sterilizing drug delivery container assemblies. The shielding member includes a housing comprising a first shielding portion and a second shielding portion. The first shielding portion includes a first surface, a second surface opposite the first surface, and a plurality of first bore portions extending between the first and second surfaces. The second shielding portion has a first surface and a second surface opposite the first surface and a plurality of second bore portions corresponding to and aligned with the plurality of first bore portions. The first surface of the second shielding portion coupled to the second surface of the first shielding portion. The first and second bore portions cooperate to form a plurality of receptacles including a plurality of openings in the first surface of the first shielding portion of the housing, and the receptacles are sized and configured to receive drug delivery container assemblies, each comprising a container with a container contact region and a seal member disposed adjacent the container contact region to seal the contents of the container at a sealing interface, such that each drug delivery container assembly is exposed out of the housing through one of the openings.

In another aspect, the present disclosure provides a shielding member for use in sterilizing drug delivery container assemblies including a housing comprising a first shielding portion and a second shielding portion. The first shielding portion includes a first surface, a second surface opposite the first surface, and a first bore portion extending between the first and second surfaces. The second shielding portion has a first surface and a second surface opposite the first surface, the first surface of the second shielding portion coupled to the second surface of the first shielding portion, and a second bore portion corresponding to and aligned with the first bore portion. The first and second bore portions cooperate to form a receptacle including an opening in the first surface of the first shielding portion of the housing. The receptacle is sized and configured to receive a drug delivery container assembly comprising a container with a container contact region and a seal member disposed adjacent the container contact region to seal the contents of the container at a sealing interface, such that the drug delivery container assembly is exposed out of the housing through the opening.

BRIEF DESCRIPTION OF THE DRAWINGS

The above needs are at least partially met through provision of the flow adapter for a drug delivery device described in the following detailed description, particularly when studied in conjunction with the drawings, wherein:

FIG. 5 illustrates a cross-sectional assembled view of the container assembly disposed within a housing in accordance with various embodiments;

FIG. 6 illustrates a cross-sectional assembled view of an alternative container assembly and housing in accordance with various embodiments;

FIGS. 8 and 9 illustrate perspective and cross-sectional views, respectively, of an alternative embodiment of a shielding member in accordance with the principles of the present disclosure.

Skilled artisans will appreciate that elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present invention. Also, common but well-understood elements that are useful or necessary in a commercially feasible embodiment are often not depicted in order to facilitate a less obstructed view of these various embodiments. It will further be appreciated that certain actions and/or steps may be described or depicted in a particular order of occurrence while those skilled in the art will understand that such specificity with respect to sequence is not actually required. It will also be understood that the terms and expressions used herein have the ordinary technical meaning as is accorded to such terms and expressions by persons skilled in the technical field as set forth above except where different specific meanings have otherwise been set forth herein.

DETAILED DESCRIPTION

The present disclosure generally relates to systems and approaches for sterilizing a container for a drug delivery device. Generally, the container is coupled to a stopper and a crimping device to form a sealed unit and the sealed unit is disposed within a shield member. Electron Beam (referred to as "E-Beam") Irradiation is applied to the sealed unit to sterilize a contact surface between the container and the stopper which is contained within the crimping device. By advantageously relying on the geometry of the sealed unit and the shield member, suitable irradiation may reach the contact surface for the purpose of providing sterilization, while the shield member, the crimping device, and/or the stopper may act, individually or cooperatively, to limit penetration of the irradiation beams, that is, to avoid exposing the container and drug contacting surfaces to ionizing irradiation that could impact its physical, chemical, or aesthetic attributes. As such, the irradiation is shielded from the remainder of the container, thereby reducing and/or eliminating the potential for discoloration to the container, the drug that may be contained therein, and/or any other components. As a result, a user may properly inspect the contents of the container prior to drug administration, thereby reducing the number of unnecessarily disposed containers.

Figure 1:
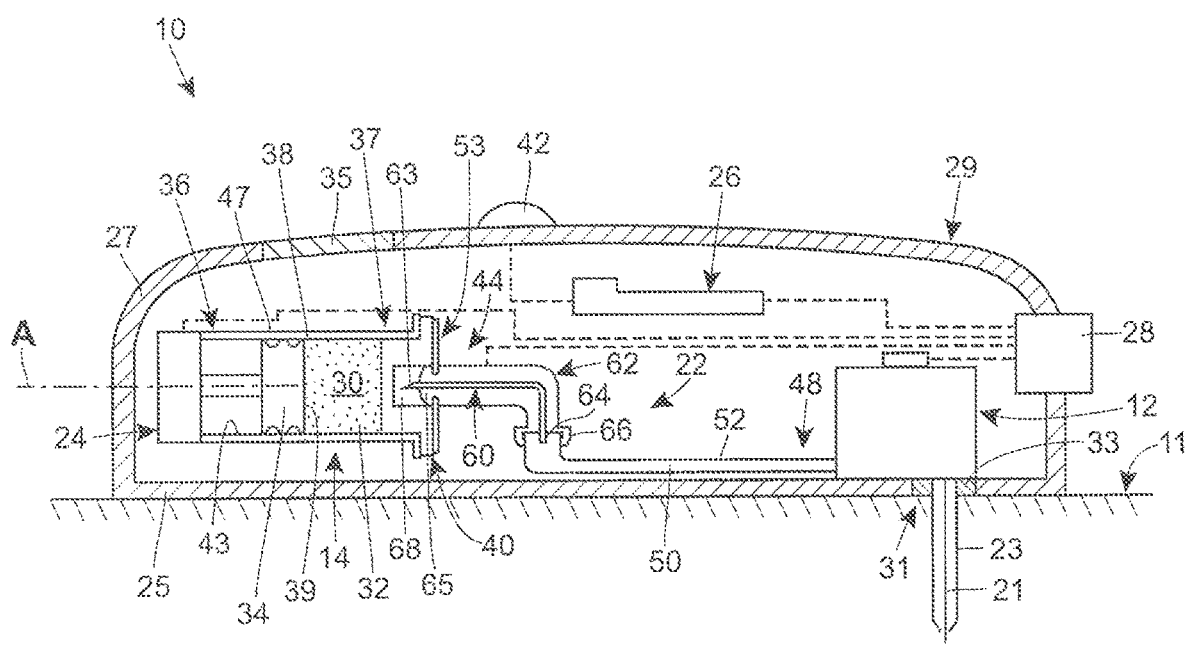
FIG. 1 illustrates a schematic cross-sectional view of an embodiment of a drug delivery device in accordance with various embodiments.

FIG. 1 is a schematic illustration of one embodiment of a drug delivery device 10 constructed in accordance with principles of the present disclosure. The drug delivery device 10 may be operated to subcutaneously or transdermally deliver a drug to a patient. In the illustrated embodiment, the drug delivery device 10 is configured as a wearable drug delivery device, such as an on-body injector or an ambulatory infusion pump, and is releasably attachable to the patient's tissue 11 (e.g., the patient's skin). In other embodiments (not illustrated), the drug delivery device 10 may be configured as a pen-type injector, such as an auto-injector or injection pen, which is temporarily held against the patient's tissue 11 over the course of the injection. The drug delivery device 10 may be configured to automatically deliver a fixed or a patient/operator-settable dose of the drug over a controlled or selected period of time. Furthermore, the drug delivery device 10 may be intended for self-administration by the patient, or may be operated by a formally trained healthcare professional or other caregiver to administer the injection.

Generally, the drug delivery device 10 may include an insertion mechanism 12, a container assembly 14 including a container 15, a fluid pathway assembly 22, a drive mechanism 24, and a controller 26, each of which may be disposed within an interior space of a main body 29. An actuator 28 (e.g., a user-depressible button, touchscreen, microphone, etc.) may protrude through or otherwise be disposed at an exterior surface of the body 29 and may be configured to initiate operation of the drug delivery device 10 by activating, via mechanical and/or electrical means (shown in dotted lines in FIG. 1), the insertion mechanism 12, the fluid pathway assembly 22, the drive mechanism 24, the controller 26, and/or other mechanisms and/or electronics. In embodiments where the actuator 28 is a button that is depressed or otherwise physically moved by a user or patient, the actuator 28 may be configured to exert a motive force needed to activate the insertion mechanism 12, the fluid pathway assembly 22, the drive assembly 24, the controller 26, and/or other mechanisms. In such embodiments, the actuator 28 may be physically connected to, either directly or indirectly via a mechanical linkage, the insertion mechanism 12, the drive mechanism 24, the fluid pathway assembly 22, and/or other mechanisms such that manually depressing or otherwise interacting with the actuator 28 supplies the motive force necessary to activate the insertion mechanism 12, the drive mechanism 24, the fluid pathway assembly 22, and/or other mechanisms. For example, in some embodiments, manually depressing the actuator 28 may cause the fluid pathway assembly 22 to move towards the stationary container assembly 14, or cause the container assembly 14 to move towards the stationary fluid pathway assembly 22, and thereby cause a container access needle to penetrate through a seal member into a reservoir or interior volume of the container assembly 14. Additionally or alternatively, the actuator 28 may operate as an input device that transmits an electrical and/or mechanical signal to the controller 26, which in turn may execute programmable instructions to control operation of the insertion mechanism 12, the drive mechanism 24, the fluid pathway assembly 22, and/or other mechanisms. In such embodiments, the controller 26 may include a processor (e.g., a microprocessor) and a non-transitory memory for storing the programmable instructions to be executed by the processor. Furthermore, in such embodiments, the drug delivery device 10 may include an internal actuator (e.g., an electric motor, a pneumatic or hydraulic pump, and/or a source of pressurized gas or liquid) which is separate from the actuator 28 and which, in response to an electrical control signal received from the controller 26, exerts the motive force needed to activate the insertion mechanism 12, the drive mechanism 24, the fluid pathway assembly 22, and/or other mechanisms.

The body 29 may include a bottom wall 25 configured to be releasably attached (e.g., adhered with an adhesive) to the patient's tissue 11, and a top wall 27 including one or more visual indicators 42 (e.g., lights, graphical displays, etc.) and/or a window 35 for viewing the container 15 and a drug 32 contained therein. The one or more visual indicators 42 may be used to communicate information to the user about the operational state of the drug delivery device 10 and/or the condition of the drug 32. An opening 31 may be formed in the bottom wall 25, and optionally a pierceable sterile barrier 33, such as a pierceable septum, may extend across the opening 31 to seal the interior of the body 29 prior to use. In some embodiments, the pierceable sterile barrier 33 may be omitted, and instead a removable sealing member (not illustrated) may cover and seal close the opening 31 prior to use.

More particularly with respect to the window 35, this element may be constructed of a transparent or semi-transparent material and generally aligned with the container 15, so as to allow a patient or user of the drug delivery device 10 to inspect the drug 32 within the container 15 and/or confirm dose completion. Suitable materials for constructing the window 35 include, but are not limited to, glass and/or plastic. The location of the window 35 on the exterior of the drug delivery device 10 may expose the drug 32 to ambient light including sunlight. Some drugs may be sensitive to certain wavelengths of light and undergo undesirable molecular changes when exposed to such wavelengths of light. For example, some drugs may be sensitive to wavelengths of light in the ultraviolet (UV) range, the visible range, and/or the infrared range. To protect drugs that are primarily sensitive to light in the UV range and/or the infrared range, a dark tint may be added to the window 35 and/or the window 35 may be dimensioned to cover a relatively small surface area of the body 29. For drugs that are primarily sensitive to light in the visible range, it may not be necessary to add a dark tint to the window 35 and/or shrink the size of the window 35. Instead, the window 35 may be constructed with a polarized filter. In some embodiments, the polarized filter may be a film or other coating that is applied to the window 35. In other embodiments, the polarized filter may be integrated directly into the material of window 35. The polarized filter may allow for viewing and inspection of the drug 32 within the container 15, while filtering out up to and including approximately (e.g., ±10%) 50% of light in the visible range. In some embodiments, the portion of visible light filtered out by the window 35 may fall in a range between approximately (e.g., ±10%) 0-50%, or 10-50%, or 20-50%, or 25-50%, or 0-40%, or 0-30%, or 0-25%, depending on the photosensitivity of the drug 32 and/or the eye strength of the patient population of the drug 32, among other considerations. Adding the polarized filter to the window 35, in lieu adding a dark tint to the window 35 and/or shrinking the size of the window 35, advantageously protects the drug 35 from light in the visible range without substantially compromising the ability of the patient or user of the drug delivery device 10 to inspect the drug 32 within the container 15.

After the bottom wall 25 of the body 29 is attached to the patient's tissue 13, the insertion mechanism 12 may be activated to move a delivery member from a retracted position within the body 29 to a deployed position extending outside of the body 29. In the present embodiment, this may include the insertion mechanism 12 inserting a trocar 21 and a hollow cannula 23 surrounding the trocar 21 through the pierceable sterile barrier 33 and into the patient's tissue 11, as illustrated in FIG. 1. Immediately or shortly thereafter, the insertion mechanism 12 may automatically retract the trocar 21, leaving the distal open end of the cannula 23 inside the patient for subcutaneous delivery of the drug 32. The trocar 21 may be solid and have a sharpened end for piercing the patient's skin 11. Furthermore, the trocar 21 may be made of a material that is more rigid than the cannula 23. In some embodiments, the trocar 21 may be made of metal, whereas the cannula 23 may be made of plastic or another polymer. The relative flexibility of the cannula 23 may allow it to be disposed subcutaneously within the patient's tissue 11 for a period of a time without causing pain or significant discomfort to the patient. In other embodiments (not illustrated), the trocar 21 and cannula 23 may be omitted, and instead the insertion mechanism 12 may insert only a rigid, hollow needle into the patient for subcutaneous delivery of the drug 32.

In some embodiments, the insertion mechanism 12 may include one or more springs (e.g., coil springs, torsion springs, etc.) initially retained in an energized state, and which are released upon depression of the actuator 28 in order to insert the trocar 21 and cannula 23, or hollow needle, into the patient. Furthermore, retraction of the trocar 21 may be achieved by the automatic release of another spring after the trocar 21 and cannula 23 have been inserted into the patient. Other power sources for insertion and/or retraction are possible, including, for example, an electric motor, a hydraulic or pneumatic pump, or a canister that releases a pressurized gas or pressurized liquid to provide actuation energy.

Figure 2A:
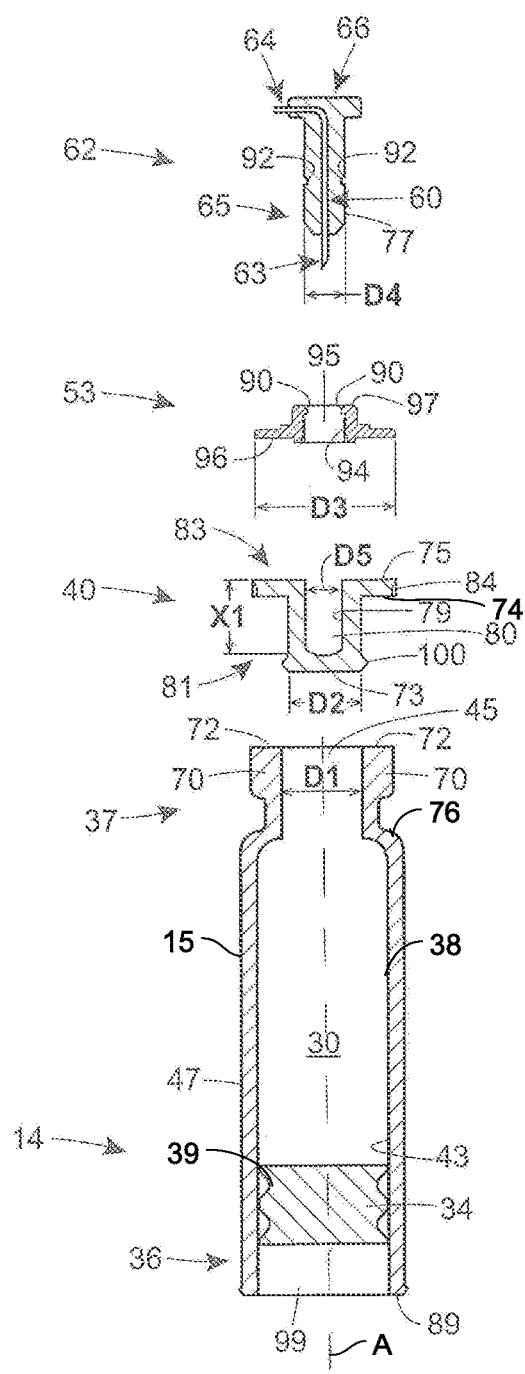
FIG. 2A illustrates a cross-sectional exploded view of an example container assembly of the example drug delivery device of FIG. 1 in accordance with various embodiments.
Figure 2B:
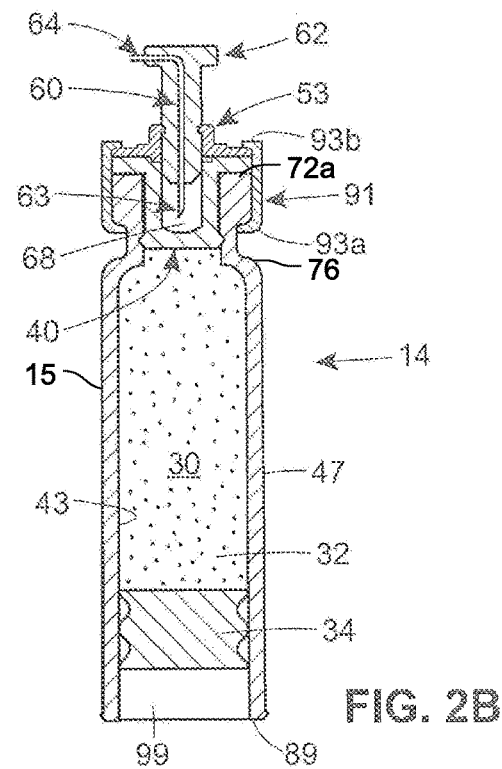
FIG. 2B illustrates a cross-sectional assembled view of a storage state of the container assembly of FIG. 2A in accordance with various embodiments.
Figure 2C:
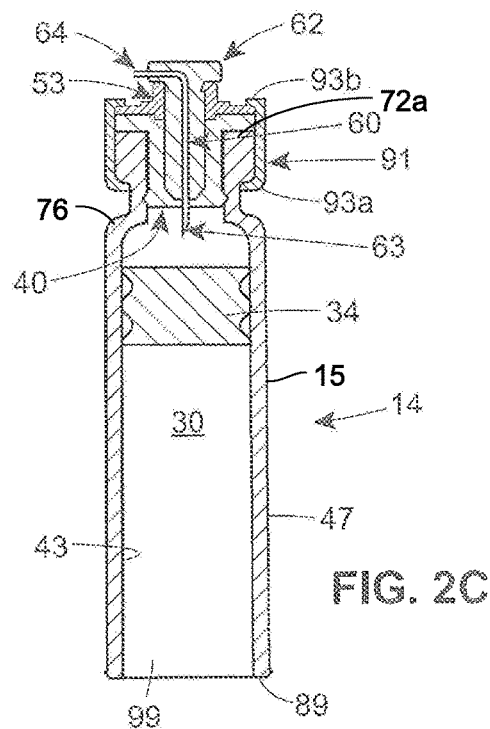
FIG. 2C illustrates a cross-sectional assembled view of a delivery state of the container assembly of FIGS. 2A and 2B in accordance with various embodiments.
Figure 3:
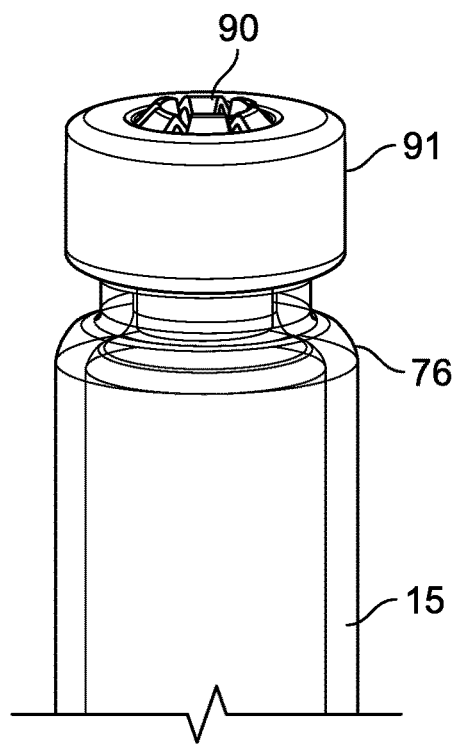
FIG. 3 illustrates a perspective assembled view of the container assembly of FIGS. 2A-2C in accordance with various embodiments.

With reference to FIGS. 1-2C, the container assembly 14 includes a container 15, which in some contexts may be referred to as a primary container, a seal member 40, and a coupling device 91. The container assembly 14 may include a proximal or first end 36 and a distal or second end 37 at which the seal member 40 and the coupling device 91 are positioned. The container 15 has an elongated portion or wall 38 extending between the first end 36 and the second end 37. The wall 38 has an interior surface 43 defining an inner volume or reservoir 30 that is filled with the drug 32 and further may have an exterior surface 47. In some embodiments, the reservoir 30 may be pre-filled with the drug 32 by a drug manufacturer prior to installation of the container 15 in the drug delivery device 10. In some embodiments, the container 15 may be rigidly connected to the body 29 such that the container 15 cannot move relative to the housing; whereas, in other embodiments, the container 15 may be slidably connected to the body 29 such that the container 15 can move relative to the body 29 during operation of the drug delivery device 10. The container 15 may have an elongate, barrel-like or cylindrical shape extending along a longitudinal axis A. In embodiments where the drug delivery device 10 is configured as an on-body injector, the longitudinal axis A of the container 15 may be perpendicular or substantially perpendicular, or otherwise non-parallel, to a direction in which the insertion mechanism 12 inserts a delivery member such as the cannula 23 into the patient. This configuration may allow the on-body injector to have a generally planar, low-profile shape that can be worn by the patient without impeding the patient's movement. Initially, a stopper 34 or other piston member may be positioned in the reservoir 30 at the proximal or first end 36 of the container 15. The stopper 34 may sealingly and slidably engage the interior surface 43 of the wall 38 of the container 15, and may be movable relative to the wall 38 of the container 15.

The volume of the drug 32 contained in the reservoir 30 prior to delivery may be: any volume in a range between approximately (e.g., ±10%) 0.5-20 mL, or any volume in a range between approximately (e.g., ±10%) 0.5-10 mL, or any volume in a range between approximately (e.g., ±10%) 1-10 mL, or any volume in a range between approximately (e.g., ±10%) 1-8 mL, or any volume in a range between approximately (e.g., ±10%) 1-5 mL, or any volume in a range between approximately (e.g., ±10%) 1-3.5 mL, or any volume in a range between approximately (e.g., ±10%) 1-3 mL, or any volume in a range between approximately (e.g., ±10%) 1-2.5 mL, or any volume in a range between approximately (e.g., ±10%) 1-2 mL, or any volume equal to or less than approximately (e.g., ±10%) 4 mL, or any volume equal to or less than approximately (e.g., ±10%) 3.5 mL, or any volume equal to or less than approximately (e.g., ±10%) 3 mL, or any volume equal to or less than approximately (e.g., ±10%) 2.5 mL, or any volume equal to or less than approximately (e.g., ±10%) 2 mL, or any volume equal to or less than approximately (e.g., ±10%) 1.5 mL, or any volume equal to or less than approximately (e.g., ±10%) 1 mL. The reservoir 30 may be completely or partially filled with the drug 32. The drug 32 may be one or more of the drugs described below, such as, for example, a granulocyte colony-stimulating factor (G-CSF), a PCSK9 (Proprotein Convertase Subtilisin/Kexin Type 9) specific antibody, a sclerostin antibody, or a calcitonin gene-related peptide (CGRP) antibody.

During operation of the drug delivery device 10, the drive mechanism 24 may push the stopper 34 along the longitudinal axis A from the proximal end 36 of the container 15 to the distal end 37 of the container 15 in order to expel the drug 32 from the container 15. In some embodiments, the drive mechanism 24 may include one or more springs (e.g., coil springs, torsion springs, etc.) initially retained in an energized state, and which are released upon depression of the actuator 28. Following their release, the spring(s) may expand or contract to move the stopper 34 through the reservoir 30 along the longitudinal axis A from the proximal end 36 of the container 15 to the distal end 37 of the container 15. In other embodiments, the drive mechanism 24 may include an electric motor (not illustrated) which rotates a gear mechanism, including for example one or more sprocket gears, to cause axial motion of the stopper 34 through the reservoir 30. In still further embodiments, the drive mechanism 24 may include both an electric motor and spring(s), wherein the electric motor regulates expansion of the spring(s) via a tether or pulley system. In still further embodiments, the drive mechanism 24 may include a canister that releases a pressurized gas or pressurized liquid to provide actuation energy.

At the distal end 37 of the container 15, an opening 45 (see FIG. 2A) may be formed in a container contact region or distal end surface 72 (see FIG. 2A) of the wall 38. The container contact region 72 may define a portion of the exterior surface 47 of the wall 38. At least prior to operation of the drug delivery device 10, the opening 45 may be covered and sealed closed by the seal member 40, such as a pierceable septum, connected to the distal end 37 of the container 15. The seal member 40 may include a proximal end surface 73, a seal member contact region 74, and a distal end surface 75. The proximal end surface 73 of the seal member 40 and the interior surface 43 of the wall 38 of the container 15 may define the reservoir 30. Additionally, in some embodiments, a distal end surface 39 of the stopper 34 may define the reservoir 30.

Generally, the seal member 40 may be configured to selectively permit access to the reservoir 30. During operation, the seal member 40 may be physically altered (e.g., pierced) to permit access to and fluid communication with the drug 32 in the reservoir 30. In some embodiments, the seal member 40 may be constructed of a flexible or elastically deformable material such as rubber, for example, which is capable of being penetrated or pierced by a sharpened end or point 63 of a container access needle 60 of the fluid pathway assembly 22. In some embodiments, the seal member 40 may be clamped or otherwise secured to the container contact region 72 of the wall 38 by the coupling device 91 (see FIG. 2B-FIG. 4) and/or adhered directly to the container contact region 72.

Referring back to FIG. 1, fluid pathway assembly 22 may be configured to establish fluid communication between the container 15 and the insertion mechanism 12 via a sterile fluid flow path during operation of the drug delivery device 10. Prior to use of the drug delivery device 10, the fluid pathway assembly 22 may not be in fluid communication with the container 15. During setup of the drug delivery device 10, or during the initial stages of operation of the drug delivery device 10 prior to drug delivery, the user may manually, or the drug delivery device 10 may automatically, enable, connect, or open the necessary connections to establish fluid communication between the container 15 and the fluid pathway assembly 22. Subsequently, the drive mechanism 24 may move the stopper 34 in the distal direction to force the drug 32 stored in the container 15 through the sterile fluid flow path of the fluid pathway assembly 22 and into the cannula 23 or needle or other delivery member of the insertion mechanism 12 for subcutaneous delivery to the patient.

In some embodiments, the fluid pathway assembly 22 may be rigidly connected to the body 29 of the drug delivery device 10 such that the fluid pathway assembly 22 cannot move relative to the housing; whereas, in other embodiments, the fluid pathway assembly 22 may be slidably or moveably connected to the body 29 such that the fluid pathway assembly 22 can move relative to the body 29 during operation of the drug delivery device 10. In the former embodiments, the container 15 may be slidably or moveably connected to the body 29 such that the seal member 40 can be moved toward and pierced by the point 63 of the stationarily arranged container access needle 60 of the fluid pathway assembly 22. In the latter embodiments, the container 15 may be stationarily positioned while the fluid pathway assembly 22 is moved toward the container 15, causing the point 63 of the container access needle 60 to pierce through the seal member 40 and access the reservoir 30.

The fluid pathway assembly 22 may include a first end 44 connected to the container 15, a second end 48 connected to the insertion mechanism 12, and a fluid passage 50 extending between the first end 44 and the second end 48. As described in more detail below, in some embodiments the first end 44 of the fluid pathway assembly 22 may be connected to the container 15 via a clip member 53. The fluid passage 50 may be sterilized, and may be partially or entirely made of a flexible tubing 52. Initially, there may be slack in the flexible tubing 52 to allow the fluid pathway assembly 22 to move relative to the body 29 and/or to allow components of the insertion mechanism 12 to which the fluid pathway assembly 22 is attached to move relative to the body 29. In some embodiments, the fluid passage 50 may include a rigid fluid restrictor element (not illustrated) in addition to the flexible tubing 52. The fluid restrictor element may have a smaller inner diameter than that of the flexible tubing 52 in order to regulate the flow rate of the drug 32 as it passes through the fluid pathway assembly 22. Furthermore, the fluid restrictor element may be made of a more rigid material than the flexible tubing 52. For example, the fluid restrictor element may be made of metal, whereas the flexible tubing 52 may be made of a polymeric material such as plastic.

Still referring to FIG. 1, the first end 44 of the fluid pathway assembly 22 may include the container access needle 60 and an overmold member 62. In general, the overmold member 62 may serve as a mounting member or connection hub for the container access needle 60 and provide a portion of the container access needle 60 which does not access the reservoir 30 with an enlarged outer dimension, such as an enlarged outer diameter. The container access needle 60 may have a sharpened end or point 63, corresponding to a proximal end of the container access needle 60, and a distal end 64 in fluid communication with the fluid passage 50. In the illustrated embodiment, the container access needle 60 has a bend such that the point 63 of the container access needle 60 may be axially aligned with the longitudinal axis A of the container 15 whereas the distal end 64 of the container access needle 60 may be perpendicular or otherwise non-parallel to the longitudinal axis A of the container 15. The overmold member 62 may cover a length of the container access needle 60, including the bend, with the point 63 of the container access needle 60 protruding outwardly from a proximal end 65 of the overmold member 62. As shown in FIG. 1, a distal end 66 of the overmold member 62 may include a mouth or opening that allows an end of the flexible tubing 52 to be inserted into the overmold member 62. In alternative embodiments, the distal end 66 of the overmold member 62 may be inserted into an opening formed in the end of the flexible tubing 52.

The container access needle 60 may possess a hollow, tubular shape with one or more openings at each of the point 63 and the distal end 64. The container access needle 60 made be constructed of a rigid material including, but not limited to, metal (e.g., stainless steel) and/or plastic. In some embodiments, the overmold member 62 may be constructed of a different material than the container access needle 60 such that the overmold member 62 and the container access needle 60 are separate, but rigidly connected components. In some embodiments, the overmold member 62 may be constructed of a rigid plastic material whereas the container access needle 60 is constructed of metal. In other embodiments, the overmold member 62 and the container access needle 60 may be made of the same material such that they form a single, unitary one-piece structure.

Generally, the overmold member 62 may have a sleeve-like or tubular shape that surrounds a length of the container access needle 60. The overmold member 62 may be fixedly or rigidly connected to the needle 60 such that the overmold member 62 and the needle 60 can move together jointly as a single unit or structure. Stated another way, the overmold member 62 may be fixedly or rigidly connected to the container access needle 60 such that the needle 60 is prevented from moving relative to the overmold member 62. In some embodiments, the fixed or rigid connection between the overmold member 62 and the container access needle 60 may be achieved by having the material of the overmold member 62 bond to the material of the container access needle 60. Such bonding may be achieved by forming the overmold member 62 around the container access needle 60 by way of an overmolding or insert molding process. In some such embodiments, the container access needle 60 may be placed in a mold and subsequently a melted plastic, or other melted material, may be poured or injected into the mold and allowed to solidify to form the overmold member 62. Other processes for manufacturing the overmold member 62 are possible as well. In alternative embodiments, the overmold member 62 may be formed with a through hole or passage extending between the proximal and distal ends 65 and 66 and subsequently the container access needle 60 may be inserted into this through hole or passage. In such embodiments, the container access needle 60 may be secured to the overmold member 62 via, for example, an interference-fit connection, an adhesive, and/or a fastener.

At least the proximal end 65 of the overmold member 62 may flushly cover a length of the container access needle 60 with no gaps therebetween. As seen in FIG. 1, there may be a gap between the distal end 66 of the overmold member 62 and the container access needle 60 to form the mouth or opening for receiving the flexible tubing 52. In alternative embodiments, no mouth or opening may be formed in the distal end 66 of the overmold member 62 such that the no gap exists between the distal end 66 of the overmold member 62 and the container access needle 60.

As shown in FIG. 1, and described below in more detail with reference to FIGS. 2A-2C, prior to activation of the drug delivery device 10 (e.g., in a storage state), the overmold member 62 may define an enclosed clean space 68 between the overmold member 62 and the seal member 40. In some embodiments, the enclosed clean space 68 may be an empty space which has been sterilized and which may or may not be a vacuum. In other embodiments, the enclosed clean space may be a space filled with a gaseous or liquid sterilizing agent. In the embodiment illustrated in FIGS. 1-2C, a boundary (e.g., a sterile boundary) of the enclosed clean space 68 may be defined solely by an exterior surface 77 of the overmold member 62 and an interior surface 79 of the seal member 40. However, the boundary of the enclosed clean space 68 may not to be limited to surfaces of overmold member 62 and the seal member 40. In some embodiments, an O-ring (not illustrated) may be disposed around the proximal end 65 of the overmold member 62 such that the boundary of the enclosed clean space 68 is defined by an exterior surface of the O-ring in addition to the exterior surface 77 of the overmold member 62 and the interior surface 79 of the seal member 40. In still further embodiments, the boundary of the enclosed clean space 68 may be defined by an interior surface of the clip member 53, an O-ring disposed around the proximal end 65 of the overmold member 62, and the distal end surface 75 of the seal member 40. Other configurations are also possible for defining the boundary of the enclosed clean space 68.

As shown in FIGS. 1 and 2B, prior to activation of the drug delivery device 10, the container access needle 60 may be arranged in a storage position with its point 63 disposed exterior to the reservoir 30. In some embodiments, in the storage position, the point 63 of the container access needle 60 may be disposed in the enclosed clean space 68, thereby inhibiting or preventing contamination of the point 63 of the container access needle 60. In other embodiments, in the storage position, the point 63 of the container access needle 60 may be disposed partially through the seal member 40 such that the point 63 is embedded within the material of the seal member 40. Embedding the point 63 within the material of the seal member 40 may inhibit or prevent contamination of the point 63. In some embodiments, the enclosed clean space 68 may be filled with a gaseous or liquid sterilizing agent, such that during manufacturing, when the point 63 is inserted through the enclosed clean space 68, the point 63 is sterilized by the gaseous or liquid sterilizing agent.

In order to restrain the container access needle 60 in the storage position prior to activation of the drug delivery device 10, the clip member 53 may frictionally engage the exterior surface 77 of the overmold member 62. Accordingly, the clip member 53 may resist movement of the overmold member 62 in a direction toward and/or away from the seal member 40.

As illustrated in FIG. 2C, upon activation of the drug delivery device 10, the container access needle 60 may be moved from the storage position to a delivery position, where the point 63 is disposed through the proximal end surface 73 of the seal member 40 and into the reservoir 30, thereby establishing fluid communication with the reservoir 30 optionally containing the drug 32. In some embodiments, the actuator 28 may be mechanically linked or connected, directly or indirectly, to the container access needle 60 such that manual depression of the actuator 28 provides the motive force necessary for moving the container access needle 60 from the storage position to the delivery position 62. In other embodiments, as described above, an energized actuator (including, e.g., an electric motor, a pneumatic or hydraulic pump, and/or a source of pressurized gas or liquid) may be activated in response to a user's depression of the actuator 28 and provide the motive force necessary for moving the container access needle 60 from the storage position to the delivery position.

Where appropriate, any of the above-described sub-assemblies, mechanisms, components, features, functionalities, methods of manufacture, methods of use, and other aspects of the drug delivery device 10 may be replaced with and/or combined with any of the sub-assemblies, mechanisms, components, features, functionalities, methods of manufacture, methods of use, and other aspects of the drug delivery devices described in some or all of the following documents, each of which is hereby incorporated by reference in its entirety for all purposes: U.S. Pat. No. 9,061,097; U.S. Patent Application Publication No. 2017/0124284; U.S. Patent Application Publication No. 2017/0119969; U.S. Patent Application Publication No. 2017/0098058; U.S. Patent Application Publication No. 2017/0124285; U.S. Patent Application Publication No. 2017/0103186; U.S. Provisional Patent Application No. 62/460,501 entitled "INSERTION MECHANISM FOR DRUG DELIVERY DEVICE"; U.S. Provisional Patent Application No. 62/469,226 entitled "INSERTION MECHANISM FOR DRUG DELIVERY DEVICE"; U.S. Provisional Patent Application No. 62/468,190 entitled "INSERTION MECHANISM AND METHOD OF INSERTING A NEEDLE OF A DRUG DELIVERY DEVICE"; U.S. Provisional Patent Application No. 62/460,559 entitled "DRUG DELIVERY DEVICE WITH STERILE FLUID FLOWPATH AND RELATED METHOD OF ASSEMBLY"; U.S. Provisional Patent Application No. 62/294,842 entitled "DRUG DELIVERY DEVICE, METHOD OF MANUFACTURE, AND METHOD OF USE"; U.S. Provisional Patent Application No. 62/297,718 entitled "DRUG DELIVERY DEVICE, METHOD OF MANUFACTURE, AND METHOD OF USE"; U.S. Provisional Patent Application No. 62/320,438 entitled "DRUG DELIVERY DEVICE, METHOD OF MANUFACTURE, AND METHOD OF USE"; International Patent Application No. PCT/US2017/017627 entitled "DRUG DELIVERY DEVICE, METHOD OF MANUFACTURE, AND METHOD OF USE"; and International Patent Application No. PCT/US2017/026524 entitled "DRUG DELIVERY DEVICE, METHOD OF MANUFACTURE, AND METHOD OF USE".

Turning to FIGS. 2A-2C, illustrated is an enlarged view of the container 15, the seal member 40, and part of the fluid pathway assembly 22 of the drug delivery device 10 shown in FIG. 1. The container 15 may have a generally cylindrical shape with a barrel portion occupying most of the proximal end 36, and a neck portion at its distal end 37. In the depicted version, an inner diameter D1 of the distal end 37 neck portion is smaller than an inner diameter of the barrel portion. At the distal end 37 neck portion of the container 15, the wall 38 may protrude radially outwardly to define a container flange 70. The container flange 70 and the wall 38 may be connected via a curved and/or angled shoulder 76. The container flange 70 may extend partially or entirely around a circumference of the distal end 37 of the container 15. The container flange 70 may define a container contact region 72 of the container 15, which is perpendicular or otherwise non-parallel to the longitudinal axis A of the container 15 and generally faces in a distal direction. The opening 45 may be formed in the container contact region 72 and communicate with the reservoir 30 of the container 15. In some embodiments, the container flange 70 may be omitted such that the container contact region 72 does not project radially outwardly of a remainder of the container 15. The wall 38 at the proximal end 36 of the container 15 may include a proximal end surface 89, which is perpendicular or otherwise non-parallel to the longitudinal axis A of the container 15 and generally faces in a proximal direction. An opening 99 may be formed in the proximal end surface 89 and communicate with the reservoir 30. The stopper 34 may inserted through the opening 99 into the container 15. The container 15 may be constructed of glass, a polymeric material such as plastic, or any other suitably inert material which is not likely to chemically interact with the drug 32.

Referring to FIG. 2A, the seal member 40 may be centrally aligned with the longitudinal axis A of the container 15 when the seal member 40 is inserted into the container 15 such that the seal member 40 and the container 15 share the same longitudinal axis A. The seal member 40 may be divided by an imaginary plane perpendicular to the longitudinal axis A into a proximal (or bottom) end 80 and a distal (or top) end 82. The proximal end 81 and the distal end 83 may each possess a generally cylindrical shape and have outer diameters D2 and D3, respectively, as seen in FIG. 2A. The distal end 83 may be enlarged relative to the proximal end 81, such that the outer diameter D3 (or other outer dimension) of the distal end 83 is larger than an outer diameter D2 (or other outer dimension) of the proximal end 81. A flange 84 of the seal member 40 is defined by an outer peripheral (e.g., circumferential) portion of the distal end 83 of the seal member 40 that is disposed radially outwardly of the proximal end 81 of the seal member 40. The seal member contact region 74 is at least partially formed by the flange 84.

Figure 4:
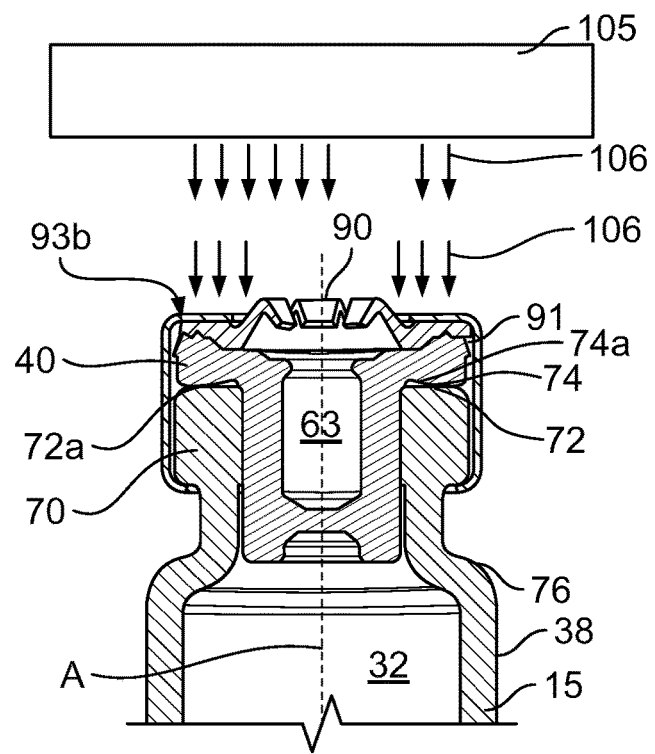
FIG. 4 illustrates a zoomed cross-sectional assembled view of the container assembly of FIGS. 2A-3 in accordance with various embodiments.
Figure 7A:
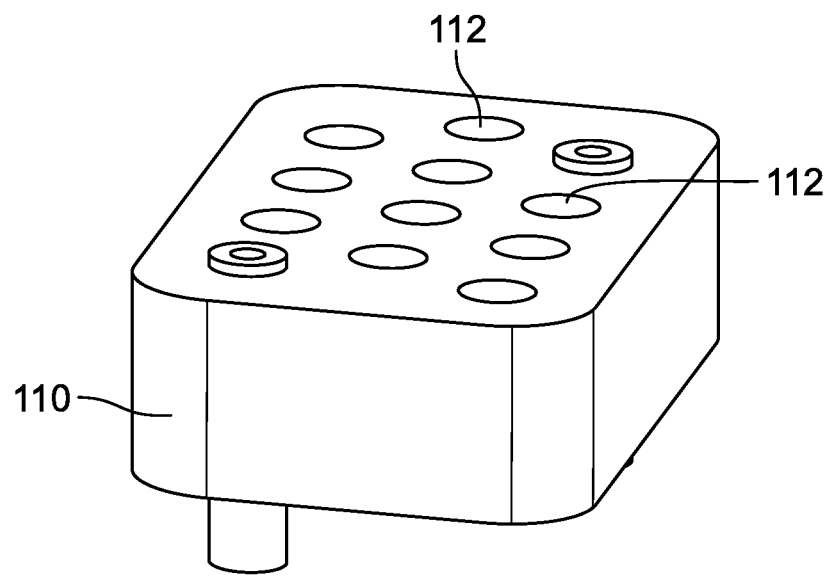
FIGS. 7A and 7B illustrate perspective views of a housing to accommodate one or more container assemblies in accordance with various embodiments.
Figure 7B:
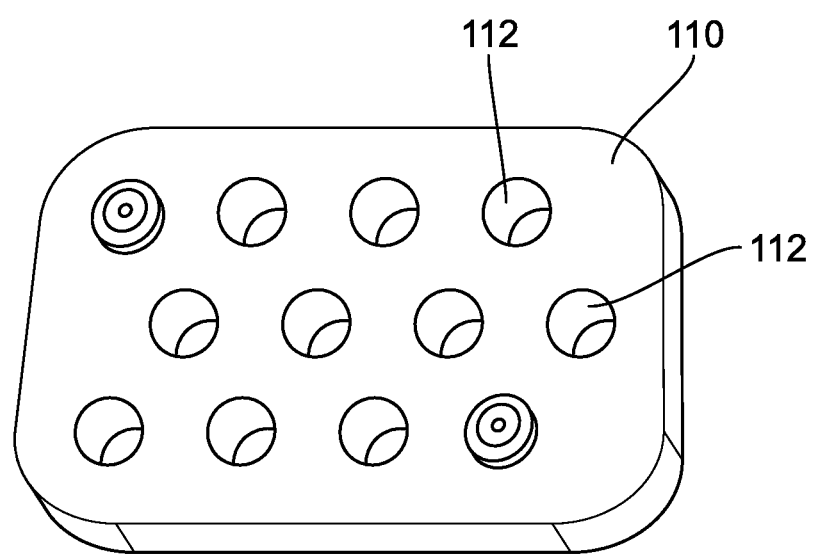

Referring to FIGS. 2B, 2C, and 4, when the seal member 40 is attached to the container 15, the proximal end 81 of the seal member 40 may be inserted through the opening 45 into the reservoir 30 and the seal member contact region 74 may directly contact and sealingly engage the container contact region 72 of the container 15 to form a sealing interface 72a. As illustrated in FIG. 4, the seal member contact region 74 may include an angled portion 74a that may compress to help form a fluid and/or airtight seal with the container contact region 72.

In some embodiments, the proximal end 81 of the seal member 40 may include one or more radially outwardly protruding annular ribs 100 for sealingly engaging the inner surface 43 of the wall 38 of the container 15. The annular rib(s) 100 may provide a secondary barrier to prevent the ingress contaminants that breach the seal between the flange 84 of the seal member 40 and the container contact region 72 of the container 70. In embodiments including the annular rib(s) 100, the outer diameter D2 of the proximal end 81 of the seal member 40 may be equal to or less than inner diameter D1 of the container 15 while the rib(s) 100 can be slightly larger than D1 in diameter such that the rib(s) 100 compress upon assembly to ensure a tight seal. In other embodiments, the annular rib(s) 100 may be omitted (see FIGS. 3A and 3B), and the outer diameter D2 of the proximal end 81 of the seal member 40 may be slightly larger than the inner diameter D1 of the container 15 to provide a tight fit and seal. In still further embodiments, the annular ribs 100 may be omitted and the outer diameter D2 of the proximal end 81 of the seal member 40 may be smaller than the inner diameter D1 of the container 15, such that there is no seal formed therebetween.

Referring back to FIG. 2A, a depression or recess 80 may be formed in the seal member 40 and dimensioned to receive the proximal end 65 of the overmold member 62. The recess 80 may start at the distal end surface 75 of the seal member 40 and extend into the seal member 40 to a position which is located in the distal direction relative to the proximal end surface 73 of the seal member 40. Accordingly, the recess 80 may define a blind bore having a depth X1. The recess 80 may be defined by an interior surface 79 of the seal member 40. In some embodiments, the recess 79 may receive the overmold member 62 via an interference-fit connection (also referred to as a press-fit connection), such that the interior surface 79 of the seal member 40 sealingly engages an exterior surface 77 of the overmold member 62 to prevent or inhibit the ingress of microbes and other contaminants. The interference-fit connection may be achieved by constructing the proximal end 65 of the overmold member 62 with an outer diameter D4 (or other outer dimension) that is larger than or equal to the inner diameter D5 (or other inner dimension) of the recess 80. The interference-fit connection may result in friction between the interior surface 79 of the seal member 40 and the exterior surface 77 of the overmold member 62 that resists movement of the overmold member 62 relative to the seal member 40. In other embodiments, the outer diameter D4 of the proximal end 65 of the overmold member 62 may be smaller than the inner diameter D5 of the recess 80, and an O-ring (not illustrated) may be disposed around the proximal end 65 of the overmold member 62 to sealingly engage the interior surface 79 of the seal member 40 to prevent or inhibit the ingress of contaminants.

Referring to FIG. 2B, the enclosed clean space 68 may be formed by inserting the proximal end 65 of the overmold member 62 partially into the recess 80, such that the proximal end 65 of the overmold member 62 does not extend the entire depth X1 into the recess 80. The resulting gap between the proximal end 65 of the overmold member 62 and the bottom of the recess 80 may correspond to the enclosed clean space 68. In this way, the enclosed clean space 68 may be defined within the recess 80.

FIG. 2B illustrates that at least a portion of the recess 80 may be disposed in a proximal direction relative to the container contact region 72 of the container 15. Accordingly, at least a portion of the recess 80 may be disposed within the container 15. Thus, when inserted into the recess 80, at least a portion of the overmold member 62 may also be disposed within the container 15. This may reduce an axial length of the overmold member 62 which is disposed exterior to the container 15, which in turn may save space within the body 29 of the drug delivery device 10. As a result, the drug delivery device 10 may be permitted to have a more compact design.

The configuration shown in FIG. 2B corresponds to a storage position or state of the container access needle 60 and the overmold member 62. The overmold member 62 may be held statically in the storage position for a period of time between the completion of assembly of the drug delivery device 10 and activation of the drug delivery device 10 by a user or patient. As shown in FIG. 2B, in the storage position, the point 63 of the container access needle 60 may be disposed in the enclosed clean space 68 and thus exterior to the reservoir 30. In other embodiments, when arranged in the storage position, the point 63 of the container access needle 60 may be disposed partially through the seal member 40 such that the point 63 is embedded within the material of the seal member 40 but nonetheless disposed exterior to the reservoir 30, as described above.

In order to prevent the tip 63 of the container access needle 60 from prematurely piercing through the seal member 40 into the reservoir 30, the clip member 53 may frictionally engage the exterior surface 77 of the overmold member 62. In some embodiments, this may be accomplished by constructing the clip member 53 with a gripping element 90 (see FIG. 2A) that is received in a corresponding groove 92 (see FIG. 2A) formed in the exterior surface 77 of the overmold member 62 in the storage state, as shown in FIG. 2B. Friction between the gripping element 90 and the groove 92 may advantageously resist movement of the overmold member 62, and thus the container access needle 60, toward and/or away from the seal member 40 prior to use of the drug delivery device 10. Upon activation of the drug delivery device 10, an actuator (e.g., the actuator 28 or an internal energized actuator) may be configured to exert a motive force overcoming the frictional force between the gripping element 90 and the groove 92, and also any frictional force between the overmold member 62 and the interior surface 79 of the seal member 40 if an interference-fit connection exists therebetween, to cause the gripping element 90 to slide out of the groove 92 and move the overmold member 62 from the storage position (FIG. 2B) to the delivery position (FIG. 2C). As a result, the point 63 of the container access needle 60 may pierce through the proximal end surface 73 of the seal member 40 into the reservoir 30, thereby establishing fluid communication with the drug 32.

In the present embodiment, the gripping element 90 may be configured as a continuous annular ridge or protrusion. In other embodiments, multiple, distinct gripping elements may be formed on the clip member 53, each of which may be received in a corresponding groove formed in the exterior surface 77 of the overmold member 62 in the storage state.

Referring back to FIG. 2A, the clip member 53 may have an interior surface 94 defining a through hole 95. The through hole 95 may extend between a proximal end surface 96 and a distal end surface 97 of the clip member 53. The proximal end surface 96 of the clip member 53 may be disposed in direct contact with the distal end surface 75 of the seal member 40. The overmold member 62 may extend entirely through the through hole 95 when assembled to the clip member 53, as illustrated in FIGS. 2B and 2C. The gripping element 90 may be disposed on or formed by the interior surface 94, such that the gripping element 90 extends radially inwardly into the through hole 95.

As illustrated in FIGS. 2B and 2C, the coupling device 91 may be configured to hold or clamp the clip member 53 to the container 15, with the seal member 40 positioned between clip member 53 and the container 15. In some embodiments, the coupling device 91 may take the form of a crimp ring that is applied to the container 15 and clip member 53 with a crimping tool. The coupling device 91 may further be adapted to apply a force against the seal member 40 that causes it to compress towards the second end 37 of the container 15. As shown in FIGS. 2B and 2C, the coupling device 91 may include radially inwardly extending flanges 93a and 93b that abut against, respectively, a proximally facing surface of the container flange 70 (or other exterior surface of the wall 38 of the container 15) and the distal end surface 97 of the clip member 53, in order to clamp or press the seal member contact region 74 of the flange 84 of the seal member 40 tightly against the container contact region 72 of the container 70. The clamping force provided by the fastener 94 may help ensure an air-tight and/or fluid-tight seal at the sealing interface 72a between the seal member contact region 74 and the container contact region 72.

Upon assembling the container assembly 14, the arrangement may be subjected to electron beam irradiation to sterilize any residual contaminants trapped within the clean space 68 and/or the sealing interface 72a. As illustrated in FIGS. 4-6, an electron beam generator 105 can be positioned above the container assembly 14 to generate a sterilizing beam 106 to penetrate any or all of the seal member 40, the coupling device 91, the overmold member 62, the clip member 53, and the sealing interface 72a (formed by the seal member contact region 74 and the container contact region 72).

In order to effectively sterilize the second end 37 of the container assembly 14, it is necessary to determine an appropriate electron energy level that will maximize penetration (or dosage) of the sterilizing beam 106 at the sealing interface 72a while approaching zero penetration for the remainder of the elongated portion or wall 38 of the container 15 to ensure the container 15 does not discolor (which would prevent inspection) or otherwise chemically react in a way that may affect drug interaction or mechanical properties of the container 15. Based on desired dimensions of the particular container assembly 14, electron beams may be used having any energy level between approximately 0.3 MeV and approximately 5.0 MeV, or any energy level between approximately 0.5 MeV and approximately 3 MeV, or any energy level between approximately 1 MeV and approximately 2 MeV, or any energy level between approximately 1.1 MeV and approximately 1.7 MeV, or any energy level equal to approximately 1.5 MeV. These energy levels may result in a consistent dose to achieve the desired sterility assurance level (SAL) or could simply be to achieve a disinfection or other desired level of bioburden reduction. Each aim, especially in conjunction with the typical bioburden levels of the particular product, would result in a specific desirable goal dose that could be anywhere from approximately 5 to approximately 50 kGy, and in one version approximately 25 kGy, across the flange site 70 or sealing interface 72a. The goal dose may be achieved through a single exposure, as discussed, or it may be achieved in multiple lower exposures separated in time that cumulatively add up to the goal dose. For example, in some versions, even multiple sub-5 kGy doses could be applied over time to ultimately achieve the desired goal dose. Other examples are possible. In some approaches, some components of the container assembly 14 may be subject to prior sterilization processes as desired. In order to achieve the desired Sterility Assurance Level (SAL) with a high reliability and confidence in accordance with current good manufacturing practices, in-situ dosimetry within the container assembly 14 may be required during development, initial validation, and routine process validation. One such dosimetry technique would be to use commercially available NIST-traceable polymer dosimetry film. The film would be cut to a custom geometry that would permit it to be placed into interface 72a during the assembly of container assembly 14 in a manner that does not materially affect the position and orientation of any other components in container assembly 14. Thus assembled, such a container would now be a 'dosimeter container' that can be included in a larger batch sterilization process, disassembled after the process to extract the dosimeter film, and have that dosimeter film measured to discern the dose delivered to that container. Using such a technique, routine process measurements can be made and validations can be carried out to ensure that the desired SAL will be achieved.

As illustrated in FIGS. 5-7B, the container assembly 14 can be at least partially disposed in a receptacle 112 of a housing 110 of a shielding member that acts as a nest to shield certain aspects of the container assembly 14 from the sterilizing beam 106. The housing 110 may include one or a plurality of receptacles 112 to accommodate one or a plurality of container assemblies 14. The housing 110 may be constructed of any number of materials generally having a low atomic number (i.e., low-Z number). For example, the housing 110 may be constructed from aluminum, ceramics such as boron nitride, polymers such as polyethylene, ABS, polystyrene, or other polymers. Such materials can advantageously minimize production of x-rays created through Bremsstrahlung irradiation that may penetrate further than the electrons and thus discolor or otherwise impact the container assembly 14.

As shown in FIGS. 5 and 6, the housing 110 in the depicted version is bifurcated into a first shielding portion 111 and a second shielding portion 113 separated by an interface 115, which may be a physical or virtual interface depending on the specific construct of the housing 110, as will be discussed more below. The first shielding portion 111 includes a first surface 111a, a second surface 111b opposite the first surface 111a, and a first bore portion 112a extending therebetween. The first bore portion 112a defines an opening 117 in the first surface 111a of the first shielding portion 111. The second shielding portion 113 has a first surface 113a, a second surface 113b opposite the first surface 113a, and a second bore portion 112b extending therebetween. The first surface 113a of the second shielding portion 113 is adjacent to the second surface 111b of the first shielding portion 111 at the interface 115. So configured, the first and second bore portions 112a, 112b are aligned with each other to define the complete receptacle 112. It should be appreciated that while FIGS. 5 and 6 depict housings 110 with only a single receptacle 112, other versions of the shielding member includes a plurality of receptacles 112, each formed by complementary first and second bore portions 112a, 112b.

In some examples, the second bore portion 112b of the second shielding portion 113 may extend completely between the first and second surfaces 113a, 113b, thereby forming a bore that extends completely through the second shielding portion 113. But in other examples, the second bore portion 112b may only extend partly through the second shielding portion 113, i.e., through the first surface 113a and into the second shielding portion 113 but short of the second surface 113b, thereby defining a blind bore or cup-shaped recess.

The first shielding portion 111 and the second shielding portion 113 cooperate to define a number of blocking regions 114 positioned near the container 15 and container assembly 14 to restrict the sterilizing beam 106 from producing incidental, off-axis, angular, and/or reflected beams which may otherwise pass through the receptacle 112 and become incident on the container assembly 14. For example, the housing 110 may include a first blocking region 114a positioned near the distal end 37 of the container assembly 14. In the illustrated example, the first blocking region 114a may include a step portion 116 to accommodate the shoulder 76 of the container 15, thereby allowing the container 15 to nest within the receptacle 112 and be properly located within the housing 110. In other words, the receptacle 112 may include portions having varying diameters to accommodate specific dimensions of the container 15. In the depicted version, for example, the first bore portion 112a of the receptacle has a diameter that is smaller than a diameter of the second bore portion 112b. In other versions, the first and second bore portions 112a, 112b can have the same diameters.

In some examples, the second end 38 of the container assembly 14 is exposed through the opening 117 in the housing 110 during the sterilization process, as depicted in FIG. 5. This configuration ensures that the sterilization beam 106 is incident on the second end 38 of the container assembly 14 to provide the intended sterilization of the sealing interface 72a and/or other components. Further, during the sterilization process, the first blocking region 114a may retard or otherwise restrict irradiation from progressing towards the first end 36 of the container 15 a distance beyond the shoulder 76. That is, the step portion 116 may restrict or shield axial propagation (i.e., in a direction that is generally parallel to axis A) of the sterilizing beam 106.

The housing 110 may further include a second blocking region 114b positioned near the elongated portion 38 of the container 15. The second blocking region 114b protects the wall 38 of the container 15 and the drug 32 from unwanted exposure to the sterilizing beam 106. In some examples, the first shielding portion 111 and the second shielding portion 113 are integrally formed, and in some examples, the first shielding portion 111 and the second shielding portion 113 are distinct parts separated at the interface 115, for example, and stacked together without coupling, or they may be coupled together via any number of suitable approaches such as, for example, hinges, fasteners, and/or clasping devices. Additionally, the first shielding portion 111 and second shielding portion 113 may each themselves be made of multiple components that may be stacked or joined together.

In some forms, the blocking regions 114 may restrict propagation of the sterilizing beam 106 in any direction (i.e., in both a direction that is generally parallel to axis A and a direction that is non-orthogonal to axis A). Specifically, the blocking regions 114a, 114b may restrict the propagation of any sterilizing beams 106 that come into contact with the housing 110 in any direction. As a result, the sterilizing beam 106 may only be permitted to propagate through the container assembly 14, and any portions of the beam reflected, both directly and indirectly, into the housing 110 will be absorbed and not reflected. The housing 110 is sufficiently thick and has sufficiently spaced holes 112 to absorb the sterilizing beams 106.

By predetermining the energy of the sterilizing beam 106, the sterilizing beam 106 will only have sufficient energy to advance to a depth that is generally near the shoulder 76 of the container 15. Accordingly, the sterilizing beam 106 will make contact with any or all of the seal member 40, the coupling device 91, the overmold member 62, the clip member 53, and the sealing interface 72a (formed by the seal member contact region 74 and the container contact region 72). In one embodiment, the sterilizing beam 106 may have a dose of approximately 25 kGy at the sealing interface 72a.

The container assembly 14, the housing 110, and the electron beam generator 105 may have any number of configurations. For example, as illustrated in the alternative embodiment presented in FIG. 6, the shoulder 76 may be pronounced due to the use of a flange 70 that is substantially narrower than the remainder of the container 15. In this embodiment, the housing 110 includes a first receptacle 112a having a first diameter and a second receptacle 112b having a second diameter that is substantially greater than the first diameter. However, in some embodiments (not shown), the receptacle 112 may have a constant diameter throughout its entire length.

In still other embodiments, the housing can be constructed to have a side-shielding portion. For example, FIGS. 8 and 9 depict one alternative housing 210 used in conjunction with a storage tub 201 for containing a plurality of container assemblies 14. The housing 210 in the depicted version includes a pair of stacked plates 203a, 203b, but could include a single plate or more than a pair of plates. The housing 210 includes a first shielding portion 211 and a second shielding portion 213. The first shielding portion 211 includes generally flat plate portion with a first surface 211a, a second surface 211b opposite the first surface 211a, and a plurality of bores 212a extending therebetween. Each bore 212a defines an opening 217 in the first surface 211a of the first shielding portion 211. The second shielding portion 213 extends from a perimeter of the first shielding portion 211 downward at an angle α relative to horizontal. So configured, the second shielding portion 213 acts as a side-shielding member when the assembly is loaded into the tub 201 as shown in FIG. 9. Specifically, as shown, a plurality of container assemblies 14 can be loaded in to the tub 201 in the upright standing orientation. Subsequently, the housing 201 can be placed into the tub 201 such that the plurality of bores 212a receive the container assemblies 14 thereby aligning the first shielding portion 211 above the container assemblies 14 to protect the container assemblies 14 from downward projected sterilizing radiation. Additionally, as can be seen in FIG. 9, a distal end 215 of the second shielding portion 213 engages and rests upon a shelf surface 203 of the tub 201, which supports the housing 210 in the tub 201 and maintains the alignment of the housing 210 relative to the container assemblies 14. Moreover, as mentioned, the second shielding portion 213 serves as a side shielding member to prevent radiation that may other reflect inside of the tub 201 and impinge upon the container assemblies 14 from the perimeter region of the tub 201.

Figure 10:
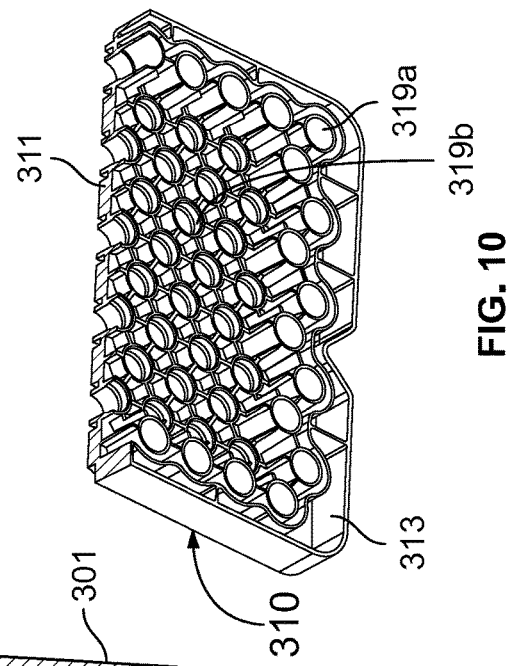
FIGS. 10 and 11 perspective and cross-sectional views, respectively, of another alternative embodiment of a shielding member in accordance with the principles of the present disclosure.
Figure 11:
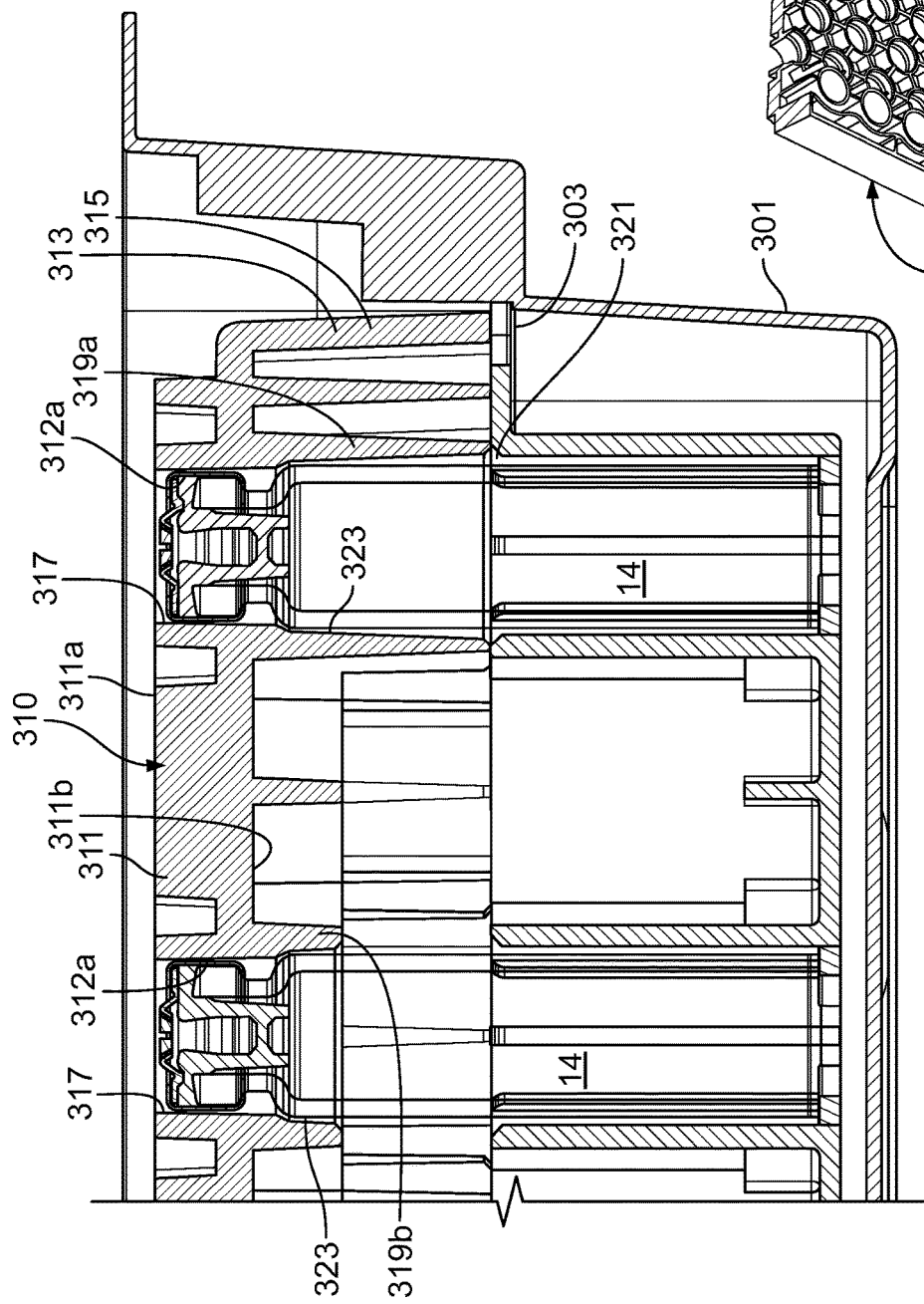

FIGS. 10 and 11 show another alternative embodiment of a housing 310 similar to that of FIGS. 8 and 9. In FIGS. 10 and 11, housing 310 is also used in conjunction with a storage tub 301 for containing a plurality of container assemblies 14. The housing 310 in the depicted version includes a single piece construction, but could include multiple pieces. The housing 310 includes a first shielding portion 311 and a second shielding portion 313. The first shielding portion 311 includes generally flat plate portion with a first surface 311a, a second surface 311b opposite the first surface 311a, and a plurality of bores 312a extending therebetween. Each bore 312a defines an opening 317 in the first surface 311a of the first shielding portion 311. The second shielding portion 313 extends from a perimeter of the first shielding portion 311 downward. So configured, the second shielding portion 313 acts as a side-shielding member when the assembly is loaded into the tub 301 as shown in FIG. 11. Specifically, as shown, a plurality of container assemblies 14 can be loaded in to the tub 301 in the upright standing orientation. Subsequently, the housing 301 can be placed into the tub 301 such that the plurality of bores 312a receive the container assemblies 14 thereby aligning the first shielding portion 311 above the container assemblies 14 to protect the container assemblies 14 from downward projected sterilizing radiation. Additionally, as can be seen in FIG. 11, a distal end 315 of the second shielding portion 313 engages and rests upon a shelf surface 303 of the tub 301, which supports the housing 310 in the tub 301 and maintains the alignment of the housing 310 relative to the container assemblies 14. Moreover, as mentioned, the second shielding portion 313 serves as a side shielding member to prevent radiation that may other reflect inside of the tub 301 and impinge upon the container assemblies 14 from the perimeter region of the tub 301. Unlike the housing in FIGS. 8 and 9, the second shielding portion 313 of the housing 310 in FIGS. 10 and 11 extends generally perpendicularly downward from horizontal and stands on the shelf surface 303 of the tub 301. But in other versions, the second shielding portion 313 could extend at an angle relative to horizontal. Another distinction is that the housing 301 in FIGS. 10 and 11 includes added side shielding protection for the individual container assemblies. That is, as can be seen in FIGS. 10 and 11, the housing 310 includes a plurality of cylindrical collars 319a and 319b extending down from the second surface 311b of the first shielding portion 311 for receiving the container assemblies 14. Interior surfaces 323 of the collards 319 can be contoured to closely fit and receive the container assemblies 14. Collars 319a are located around the perimeter of the housing 310, and collars 319b are located interior. The perimeter collars 319a are longer and cover more of the respective container assemblies 14. That is, distal ends 321 of the perimeter collars 319a can engage and rest upon the shelf surface 303 of the tub 301 same as the distal ends 315 of the second shielding portion 313. So configured, the collars 319 provide an extra added layer of protection against the possibility of radiation penetrating the housing 310 from the side perimeter of the tub 301 or otherwise.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept. For example, the container assembly 14 of the foregoing description and claims tends to resemble a cartridge for use in drug delivery devices, the disclosure is not limited in this regard. In other versions, the container assembly 14 can include a conventional vial or syringe barrel, for example, as such containers would also benefit from the teachings presented. Additionally, the means of sterilizing radiation may be selected to be principally from photons (i.e. x-rays) rather than electrons or some combination of photons and electrons. In this case, the generator 105 may be oriented similarly but have other means of generating ionizing radiation. An x-ray source may come from an electron-beam generator, or by other means. In the case where the ionizing radiation is principally x-rays, the appropriate photon (x-ray) energy level ranges will be different than those described for electrons, since photons will penetrate further through materials than electrons of the same energy level. Based on desired dimensions of the particular container assembly 14, x-ray beams may be used having any energy level between approximately 3 keV and approximately 50 keV, or any energy level between approximately 5 keV and approximately 25 keV, or any energy level between approximately 8 keV and approximately 20 keV.

Drug Information

As mentioned above, the container of the drug delivery device may be filled with a drug. This drug may be any one or combination of the drugs listed below, with the caveat that the following list should neither be considered to be all inclusive nor limiting.

For example, the container may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the container may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of sequence identification number:2 as set forth therein in FIG. 2 and/or the heavy chain of sequence identification number:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of sequence identification numbers: 305-351, including TN8-19-1 through TN8-19-40, TN8-19 con1 and TN8-19 con2; peptibodies of the mL2 family of sequence identification numbers:357-383; the mL15 family of sequence identification numbers:384-409; the mL17 family of sequence identification numbers:410-438; the mL20 family of sequence identification numbers:439-446; the mL21 family of sequence identification numbers:447-452; the mL24 family of sequence identification numbers:453-454; and those of sequence identification numbers:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2xL1(N); 2xL1(N) WT; Con4 (N), Con4 (N) 1K WT, 2xCon4 (N) 1K; L1C; L1C 1K; 2xL1C; Con4C; Con4C 1K; 2xCon4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; AbIA1; AbIF; AbIK, AbIP; and AbIP, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present disclosure are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences sequence identification number:1 and sequence identification number:7 respectively therein); 5D (having light chain variable and heavy chain variable sequences sequence identification number:2 and sequence identification number:9 respectively therein); 2H (having light chain variable and heavy chain variable sequences sequence identification number:3 and sequence identification number:10 respectively therein); 43H (having light chain variable and heavy chain variable sequences sequence identification number:6 and sequence identification number:14 respectively therein); 41H (having light chain variable and heavy chain variable sequences sequence identification number:5 and sequence identification number:13 respectively therein); and 15H (having light chain variable and heavy chain variable sequences sequence identification number:4 and sequence identification number:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of sequence identification number:17 and the light chain of sequence identification number:18; those having the heavy chain variable region of sequence identification number:6 and the light chain variable region of sequence identification number:8; those having the heavy chain of sequence identification number:19 and the light chain of sequence identification number:20; those having the heavy chain variable region of sequence identification number:10 and the light chain variable region of sequence identification number:12; those having the heavy chain of sequence identification number:32 and the light chain of sequence identification number:20; those having the heavy chain variable region of sequence identification number:30 and the light chain variable region of sequence identification number:12; those having the heavy chain sequence of sequence identification number:21 and the light chain sequence of sequence identification number:22; those having the heavy chain variable region of sequence identification number:14 and the light chain variable region of sequence identification number:16; those having the heavy chain of sequence identification number:21 and the light chain of sequence identification number:33; and those having the heavy chain variable region of sequence identification number:14 and the light chain variable region of sequence identification number:31, as disclosed in the foregoing publication. A specific antibody contemplated is antibody 1119 as disclosed in the foregoing U.S. publication and having a complete heavy chain of sequence identification number:17 as disclosed therein and having a complete light chain of sequence identification number:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising sequence identification number:8 and a light chain variable region having sequence identification number:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4ß7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor® (nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-05 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, hu-MetG-CSF); Orthoclone OKT3® (muromonab-CD3, anti-CD3 monoclonal antibody); Procrit® (epoetin alfa); Remicade® (infliximab, anti-TNFα monoclonal antibody); Reopro® (abciximab, anti-GP IIb/IIIa receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-B. anthracis protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human anti-TRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/ hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFß mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9). Such PCSK9 specific antibodies include, but are not limited to, Repatha® (evolocumab) and Praluent® (alirocumab), as well as molecules, variants, analogs or derivatives thereof as disclosed in the following patents or patent applications, each of which is herein incorporated by reference in its entirety for all purposes: U.S. Pat. Nos. 8,030,547, 8,563,698, 8,829,165, 8,859,741, 8,871,913, 8,871,914, 8,883,983, 8,889,834, 8,981,064, 9,056,915, 8,168,762, 9,045,547, 8,030,457, 8,030,457, 8,829,165, 8,981,064, 8,030,457, U.S. Publication No. 2013/0064825, U.S. Patent Application Publication No. 2012/0093818, U.S. Patent Application Publication No. 2013/0079502, U.S. Patent Application Publication No. 2014/0357850, U.S. Patent Application Publication No. 2011/0027287, U.S. Patent Application Publication No. 2014/0357851, U.S. Patent Application Publication No. 2014/0357854, U.S. Patent Application Publication No. 2015/0031870, U.S. Patent Application Publication No. 2013/0085265, U.S. Patent Application Publication No. 2013/0079501, U.S. Patent Application Publication No. 2012/0213797, U.S. Patent Application Publication No. 2012/0251544, U.S. Patent Application Publication No. 2013/0072665, U.S. Patent Application Publication No. 2013/0058944, U.S. Patent Application Publication No. 2013/0052201, U.S. Patent Application Publication No. 2012/0027765, U.S. Patent Application Publication No. 2015/0087819, U.S. Patent Application Publication No. 2011/0117011, U.S. Patent Application Publication No.

2015/0004174, U.S. Provisional Patent Application No. 60/957,668, U.S. Provisional Patent Application No. 61/008,965, U.S. Provisional Patent Application No. 61/010,630, U.S. Provisional Patent Application No. 61/086,133, U.S. Provisional Patent Application No. 61/125,304, U.S. Provisional Patent Application No. 61/798,970, U.S. Provisional Patent Application No. 61/841,039, U.S. Provisional Patent Application No. 62/002,623, U.S. Provisional Patent Application No. 62/024,399, U.S. Provisional Patent Application No. 62/019,729, U.S. Provisional Patent Application No. 62/067,637, U.S. patent application Ser. No. 14/777,371, International Patent Application No. PCT/US2013/048714, International Patent Application No. PCT/US2015/040211, International Patent Application No. PCT/US2015/056972, International Patent Application Publication No. WO/2008/057457, International Patent Application Publication No. WO/2008/057458, International Patent Application Publication No. WO/2008/057459, International Patent Application Publication No. WO/2008/063382, International Patent Application Publication No. WO/2008/133647, International Patent Application Publication No. WO/2009/100297, International Patent Application Publication No. WO/2009/100318, International Patent Application Publication No. WO/2011/037791, International Patent Application Publication No. WO/2011/053759, International Patent Application Publication No. WO/2011/053783, International Patent Application Publication No. WO/2008/125623, International Patent Application Publication No. WO/2011/072263, International Patent Application Publication No. WO/2009/055783, International Patent Application Publication No. WO/2012/0544438, International Patent Application Publication No. WO/2010/029513, International Patent Application Publication No. WO/2011/111007, International Patent Application Publication No. WO/2010/077854, International Patent Application Publication No. WO/2012/088313, International Patent Application Publication No. WO/2012/101251, International Patent Application Publication No. WO/2012/101252, International Patent Application Publication No. WO/2012/101253, International Patent Application Publication No. WO/2012/109530, and International Patent Application Publication No. WO/2001/031007, International Patent Application Publication No. WO/2009/026558, International Patent Application Publication No. WO/2009/131740, International Patent Application Publication No. WO/2013/166448, and International Patent Application Publication No. WO/2014/150983.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the drug comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the drug comprises a therapeutically effective amount of the anti-TSLP antibody designated as A5 within U.S. Pat. No. 7,982,016.

While the present disclosure has been described in connection with various embodiments, it will be understood that the present disclosure is capable of further modifications. The present disclosure is intended to cover any variations, uses, or adaptations of the disclosed subject matter following, in general, the principles of the present disclosure, and including such departures from the present disclosure as, within the known and customary practice within the art to which the present disclosure pertains.

It is noted that the construction and arrangement of the drug delivery device and its various components and assemblies as shown in the various exemplary embodiments is illustrative only. Although only a few embodiments of the subject matter at issue have been described in detail in the present disclosure, those skilled in the art who review the present disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter disclosed herein. For example, elements shown as integrally formed may be constructed of multiple parts or elements, and vice versa. Also, the position of elements may be reversed or otherwise varied, and the nature or number of discrete elements or positions may be altered or varied. Accordingly, all such modifications are intended to be included within the scope of the present disclosure as defined in the appended claims. Furthermore, the order or sequence of any process or method steps may be varied or re-sequenced according to alternative embodiments. Other substitutions, modifications, changes and omissions may be made in the design, operating conditions and arrangement of the various exemplary embodiments without departing from the scope of the present disclosure.

What is claimed is:

1. An irradiation shielding member for use in sterilizing a portion of each of the plurality of drug container assemblies by irradiation, the irradiation shielding member comprising:
   a housing comprising a first shielding portion and a second shielding portion, the first shielding portion including a first surface, a second surface opposite the first surface, and a plurality of first bore portions extending between the first and second surfaces, the second shielding portion having a first surface and a second surface opposite the first surface, the first surface of the second shielding portion coupled to the second surface of the first shielding portion, and a plurality of second bore portions corresponding to and aligned with the plurality of first bore portions, wherein the first and second bore portions cooperate to form a plurality of receptacles including a plurality of openings in the first surface of the first shielding portion of the housing, the plurality of receptacles sized and configured to receive the plurality of drug container assemblies, each of the plurality of drug container assemblies comprising a container with a drug contacting surface, a drug contact region, and a seal member disposed adjacent the container contact region to seal the contents of the container at a sealing interface, such that each of the plurality of drug container assemblies is exposed out of the housing through the openings and the container contact region and at least a portion of the seal member are disposed within the first bore portions, wherein the irradiation shielding member is configured to permit sterilization by an irradiation exposure of the sealing interface of each of the plurality of container assemblies while restricting sterilization by the irradiation exposure to the drug contacting surface of each of the plurality of container assemblies, the irradiation exposure is non-parallel relative to the first surface of the first shielding portion;

wherein the first shielding portion is a single component; and wherein each of the plurality of first bore portions has a first diameter, and each of the plurality of second bore portions has a second diameter that is greater than the first diameter.

2. The irradiation shielding member of claim 1, wherein the first shielding portion forms a blocking region to restrict a sterilizing beam from impacting the container during sterilization.

3. The irradiation shielding member of claim 1, wherein the housing is constructed from a material or materials with atomic elements having low atomic numbers.

4. The irradiation shielding member of claim 1, wherein the housing is constructed of aluminum, a ceramic, boron nitride, a polymer, polyethylene, or acrylonitrile butadiene styrene.

5. The irradiation shielding member of claim 1, wherein the first and second shielding portions are integrally connected.

6. The irradiation shielding member of claim 1, wherein the first and second shielding portions are separate components.

7. The irradiation shielding member of claim 6, wherein the first and second shielding portions are removably attached with one or more fasteners, couplers, hinges, and/or clasping devices.

8. The irradiation shielding member of claim 1, wherein the housing defines a shoulder at the interface between the first shielding portion and the second shielding portion, the shoulder for restricting propagation of a sterilizing beam during sterilization.

9. The irradiation shielding member of claim 1, wherein each of the receptacles has a longitudinal axis equal to a longitudinal axis of the drug container assemblies.

10. The irradiation shielding member of claim 1, wherein the first surface of the second shielding portion is removably coupled to the second surface of the first shielding portion.

11. An irradiation shielding member for use in sterilizing a portion of a drug container assembly by irradiation, the irradiation shielding member comprising:

a housing comprising a first shielding portion and a second shielding portion, the first shielding portion including a first surface, a second surface opposite the first surface, and a first bore portion extending between the first and second surfaces, the first bore portion being cylindrical, the second shielding portion having a first surface and a second surface opposite the first surface, the first surface of the second shielding portion coupled to the second surface of the first shielding portion, and a second bore portion corresponding to and aligned with the first bore portion, wherein the first and second bore portions cooperate to form a receptacle including an opening in the first surface of the first shielding portion of the housing, the receptacle sized and configured to receive a drug container assembly comprising a container with a drug contacting surface, a container contact region, and a seal member disposed adjacent the container contact region to seal the contents of the container at a sealing interface, such that the drug container assembly is exposed out of the housing through the opening and the container contact region and at least a portion of the seal member are disposed within the first bore portion, wherein the irradiation shielding member is configured to permit sterilization by an irradiation exposure of the sealing interface of the container assembly while restricting sterilization by the irradiation exposure to the drug contacting surface of the container assembly, the irradiation exposure is non-parallel relative to the first surface of the first shielding portion;

wherein the first shielding portion is a single component; and wherein each of the plurality of first bore portions has a first diameter, and each of the plurality of second bore portions has a second diameter that is greater than the first diameter.

12. The irradiation shielding member of claim 11, wherein the first shielding portion forms a blocking region to restrict a sterilizing beam from impacting the container during sterilization.

13. The irradiation shielding member of claim 11, wherein the housing is constructed from a material or materials with atomic elements having low atomic numbers.

14. The irradiation shielding member of claim 11, wherein the housing is constructed of aluminum, a ceramic, boron nitride, a polymer, polyethylene, or acrylonitrile butadiene styrene.

15. The irradiation shielding member of claim 11, wherein the first and second shielding portions are integrally connected.

16. The irradiation shielding member of claim 11, wherein the first and second shielding portions are separate components.

17. The irradiation shielding member of claim 16, wherein the first and second shielding portions are removably attached with one or more fasteners, couplers, hinges, and/or clasping devices.

18. The irradiation shielding member of claim 11, wherein the housing defines a shoulder at the interface between the first shielding portion and the second shielding portion, the shoulder for restricting propagation of a sterilizing beam during sterilization.

19. The irradiation shielding member of claim 11, wherein the receptacle has a longitudinal axis equal to a longitudinal axis of the drug container assembly.

* * * * *

UNITED STATES PATENT AND TRADEMARK OFFICE
CERTIFICATE OF CORRECTION

PATENT NO. : 11,305,026 B2
APPLICATION NO. : 16/179450
DATED : April 19, 2022
INVENTOR(S) : Loic Barbedette et al.

It is certified that error appears in the above-identified patent and that said Letters Patent is hereby corrected as shown below:

In the Claims

At Column 30, Line 64, "the plurality" should be -- a plurality --.

At Column 31, Line 19, "drug contact" should be -- container contact --.

At Column 31, Line 24, "through the openings" should be -- through one of the openings --.

At Column 31, Line 26, "the first" should be -- one of the plurality of first --.

At Column 32, Line 45, "greater than" should be -- greater than or equal to --.

Signed and Sealed this
Twentieth Day of December, 2022

Katherine Kelly Vidal
*Director of the United States Patent and Trademark Office*